United States Patent
Hribar

(10) Patent No.: US 10,423,071 B2
(45) Date of Patent: Sep. 24, 2019

(54) METHODS FOR PATTERNING HYDROGELS INTO MULTI-WELL PLATES

(71) Applicant: CYPRE, INC., San Francisco, CA (US)

(72) Inventor: Kolin Hribar, San Francisco, CA (US)

(73) Assignee: CYPRE, INC., San Francisco, CA (US)

(*) Notice: Subject to any disclaimer, the term of this patent is extended or adjusted under 35 U.S.C. 154(b) by 0 days.

(21) Appl. No.: 16/057,241

(22) Filed: Aug. 7, 2018

(65) Prior Publication Data

US 2018/0348637 A1 Dec. 6, 2018

Related U.S. Application Data

(63) Continuation of application No. 15/645,979, filed on Jul. 10, 2017, now Pat. No. 10,073,346.
(Continued)

(51) Int. Cl.
*G03F 7/20* (2006.01)
*G01N 33/50* (2006.01)

(52) U.S. Cl.
CPC ........... *G03F 7/20* (2013.01); *G01N 33/5008* (2013.01); *G01N 33/5088* (2013.01);
(Continued)

(58) Field of Classification Search
CPC .. G01N 33/5008; G01N 33/5088; G03F 7/20; B01L 2300/0829; B01L 2300/0893;
(Continued)

(56) References Cited

U.S. PATENT DOCUMENTS 8,501,476 B2   8/2013  Morgan et al.
8,906,684 B2   12/2014 Bhatia et al.
(Continued)

FOREIGN PATENT DOCUMENTS

EP   3007882 A1   4/2016
EP   3122559 A2   2/2017
(Continued)

OTHER PUBLICATIONS

Yang et al., Rapid Fabrication of Hydrogel Microstructures Using UV-Induced Projection Printing, 2015, Micromachines, 6, 1903-1913.
(Continued)

*Primary Examiner* — Steven Whitesell Gordon
(74) *Attorney, Agent, or Firm* — Fish IP Law, LLP

(57) ABSTRACT

The inventive subject matter provides methods for reproducibly fabricating hydrogel-based organ and tumor models inside multi-well plates. A hydrogel precursor, which can include cells, is instilled into a well. A pillar is inserted into the well to contact the hydrogel precursor with a surface that can be shaped or textured to provide a desired surface configuration or contour, for example that of a desired organoid or tumor feature. The hydrogel precursor is polymerized and the pillar removed. A second hydrogel precursor, which can contain a different cell type, is then instilled into the well and a second pillar, which can have a different configuration or texture, inserted. Subsequent polymerization generates a second hydrogel portion within the well. Polymerization can be carried out by photopolymerization. Different wells can be aligned with different, individually controlled light sources or a single, collimated light source.

19 Claims, 6 Drawing Sheets

Related U.S. Application Data

(60) Provisional application No. 62/360,178, filed on Jul. 8, 2016, provisional application No. 62/411,438, filed on Oct. 21, 2016.

(52) U.S. Cl.
CPC ............ *G03F 7/201* (2013.01); *G03F 7/2004* (2013.01); *G03F 7/7015* (2013.01)

(58) Field of Classification Search
CPC ............... C12M 23/12; C12N 2513/00; C12N 2533/30; C12N 5/0062; C12N 5/0693; C12N 5/0696
See application file for complete search history.

(56) References Cited

U.S. PATENT DOCUMENTS

| | | | |
|---|---|---|---|
| 9,267,103 B2 | 2/2016 | Lichtenberg et al. | |
| 9,488,641 B2 | 11/2016 | Gratzl et al. | |
| 9,506,907 B2 | 11/2016 | Bergkvist et al. | |
| 10,073,346 B2* | 9/2018 | Hribar | G03F 7/7015 |
| 2003/0129751 A1 | 7/2003 | Grikscheit et al. | |
| 2005/0169962 A1 | 8/2005 | Bhatia et al. | |
| 2008/0063851 A1 | 3/2008 | Jackman et al. | |
| 2012/0171744 A1 | 6/2012 | Souza | |
| 2013/0203146 A1 | 8/2013 | Ying et al. | |
| 2014/0093911 A1 | 4/2014 | Sun et al. | |
| 2014/0104150 A1 | 5/2014 | Hong et al. | |
| 2014/0322806 A1 | 10/2014 | Bennett et al. | |
| 2014/0342239 A1 | 11/2014 | Parker et al. | |
| 2015/0057184 A1 | 2/2015 | Bhatia et al. | |
| 2015/0080234 A1 | 3/2015 | Love et al. | |
| 2015/0175972 A1 | 6/2015 | Jabbari | |
| 2015/0268223 A1 | 9/2015 | Bhatia et al. | |
| 2015/0314613 A1 | 11/2015 | Murphy et al. | |
| 2016/0010054 A1 | 1/2016 | Garner et al. | |
| 2016/0115457 A1 | 4/2016 | Kim et al. | |
| 2016/0175800 A1* | 6/2016 | Murphy | B01J 19/0046 506/9 |
| 2016/0178611 A1 | 6/2016 | Han et al. | |
| 2016/0272946 A1 | 9/2016 | Shepherd et al. | |
| 2016/0289851 A1 | 10/2016 | Majdzarringhalamaraghy et al. | |
| 2016/0298087 A1 | 10/2016 | Qu et al. | |
| 2017/0067025 A1 | 3/2017 | Mehdi et al. | |

FOREIGN PATENT DOCUMENTS

| | | |
|---|---|---|
| WO | 2005110721 A1 | 11/2005 |
| WO | 2011050127 A1 | 4/2011 |
| WO | 2015149002 A1 | 10/2015 |
| WO | 2016044483 | 3/2016 |
| WO | 2016049345 A1 | 3/2016 |
| WO | 2016122323 A1 | 8/2016 |
| WO | 2016141137 A1 | 9/2016 |
| WO | 2016142323 A1 | 9/2016 |
| WO | 2016149032 A1 | 9/2016 |
| WO | 2016164562 A1 | 10/2016 |
| WO | 2015179572 A1 | 11/2016 |
| WO | 2016201577 A1 | 12/2016 |
| WO | 2017036533 A1 | 3/2017 |
| WO | 2017037295 A1 | 3/2017 |

OTHER PUBLICATIONS

Beebe et al., Functional hydrogel structures for autonomous flow control insidemicro fluidic channels, Apr. 6, 2000, Nature, 404, 588-590.

Cordey, M. et al., "Enhancing the Reliability and Throughput of Neurosphere Culture on Hydrogel Microwell Arrays", Stem Cells, vol. 26, 2008, pp. 2586-2594.

* cited by examiner

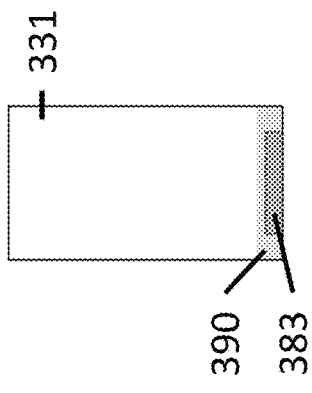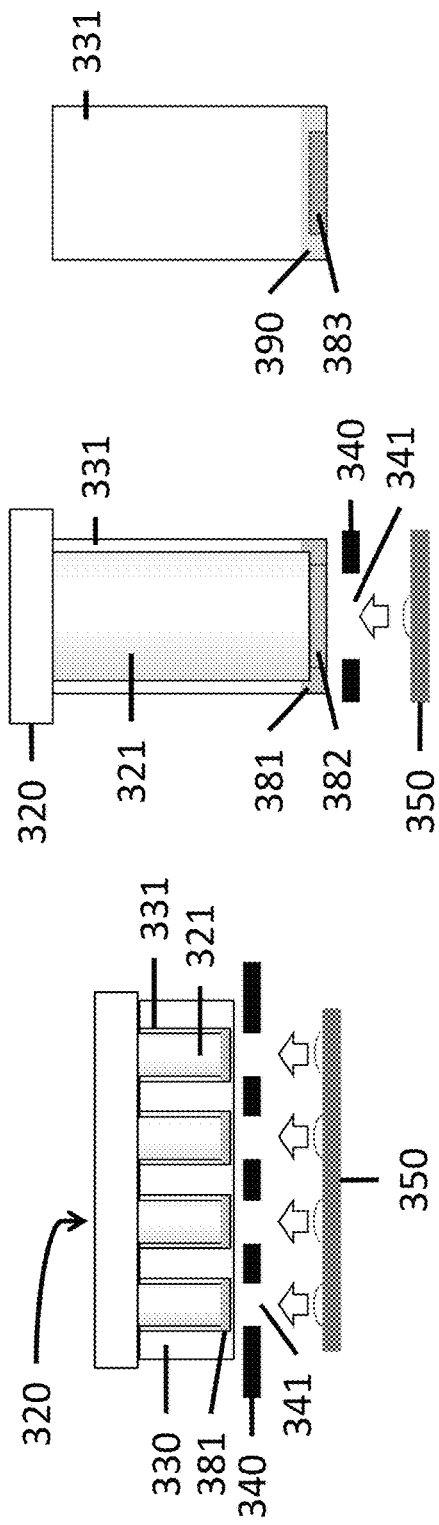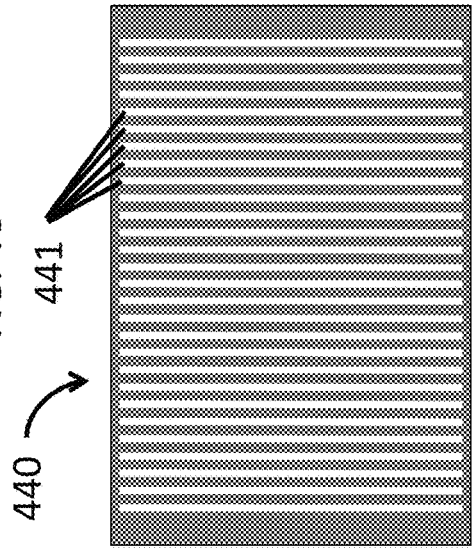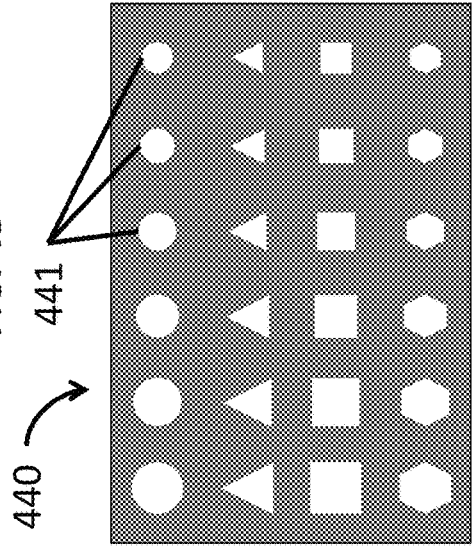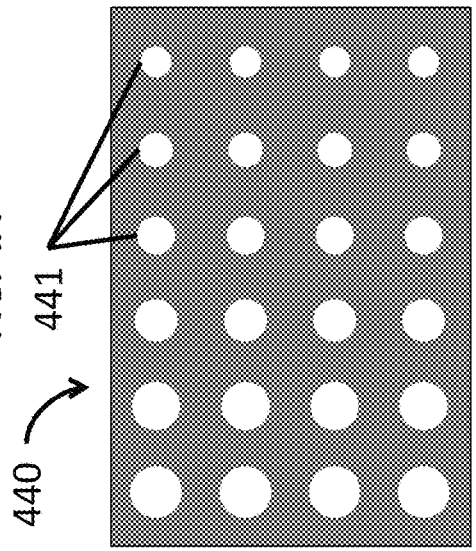

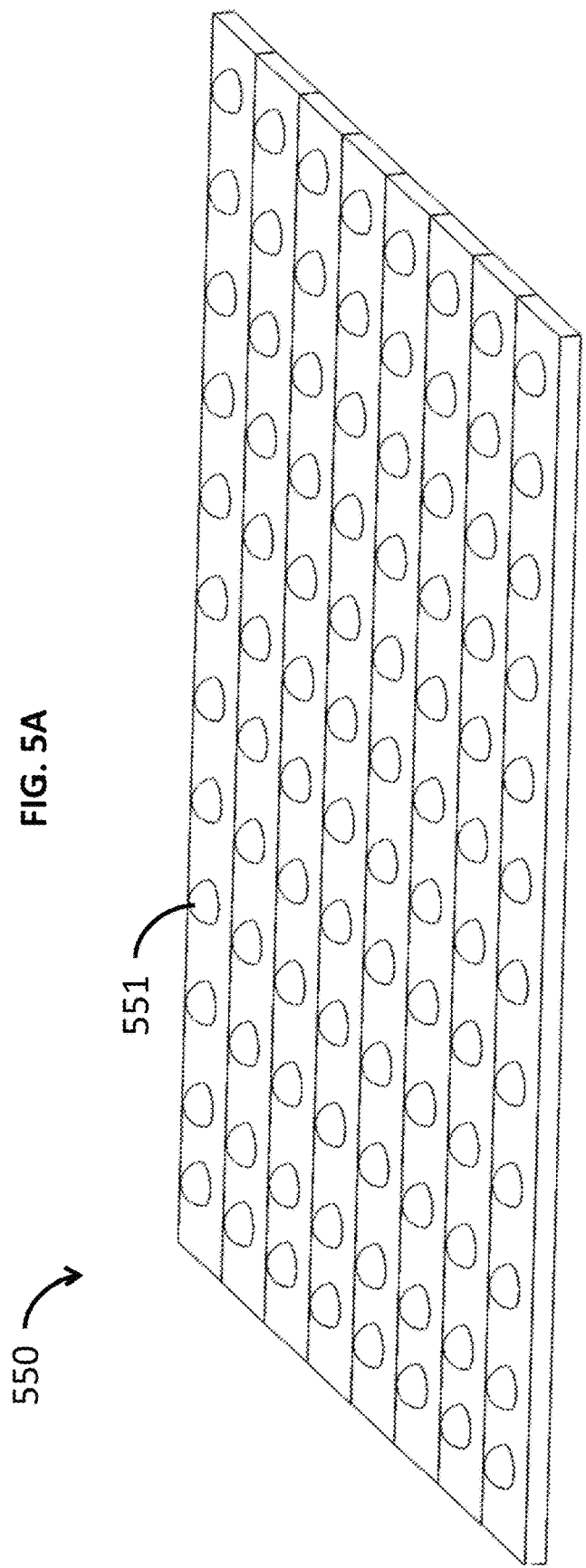

METHODS FOR PATTERNING HYDROGELS INTO MULTI-WELL PLATES

This application is a continuation of U.S. patent application Ser. No. 15/645,979, filed Jul. 17, 2017, and claims priority to U.S. provisional patent application No. 62/360,178, filed Jul. 8, 2016, and U.S. provisional patent application No. 62/411,438, filed Oct. 21, 2016. All extrinsic materials identified herein are incorporated by reference in their entirety.

FIELD OF THE INVENTION

The field of the invention is apparatuses for fabricating engineered tissues, namely tumor models, cardiac tissues, skin tissues, kidney tissues, neural tissues, liver tissues, cartilage tissues, and bone tissues for diagnostic and therapeutic screening.

BACKGROUND

The following background discussion includes information that may be useful in understanding the present invention. It is not an admission that any of the information provided herein is prior art or relevant to the presently claimed invention, or that any publication specifically or implicitly referenced is prior art.

In preclinical testing and clinical diagnostics, in vitro cellular assays are often used to test compound efficacy, toxicity, and host of other measurable outcomes related the in vivo pathological condition. For high-throughput lead compound validation experiments in preclinical screening, 96-well, 384-well, or 1536-well microtiter plates are employed to study cellular-compound interaction. Often these studies use a flat, glass or plastic (e.g., polystyrene) substrates to which cells adhere and grow in a monolayer-called two-dimensional (2D) cell culture. Such 2D cell culture techniques have demonstrated inconsistencies with the actual in vivo outcome, prompting the fields of engineering, biology, and medicine collectively to develop novel techniques to study cells at a more complex, three-dimensional (3D) physiologically relevant environment, called 3D cell culture. See e.g., W. Asghar, R. El Assal, H. Shafiee, S. Pitteri, R. Paulmurugan, U. Demirci, Engineering cancer microenvironments for in vitro 3D tumor models, *Materials Today*, 2015, 18 (10): 539-553; E. Knight, S. Przy Borski, Advances in 3D Cell Culture Technologies enabling tissue-like structures to be created in vitro, *Journal of Anatomy*, 2015, 227 (6): 746-756.

Some progress has been made using scaffold-free and scaffold-based approaches to 3D cell culture. In scaffold-free methodologies, cells aggregate into aggregates, which may have specific 3D shapes and placement. For example, multicellular sphere-like aggregates, or spheroids, form using hanging-drop and magnetic levitation methods. Spheroids also form in cultures grown in containers, such as round-bottom wells, V- and U-shaped wells on microtiter plates, and ultra-low attachment surfaces. See e.g., W. Asghar et al., supra; PCT/US2015/050522; U.S. Pat. No. 9,267,103B2; US20120171744A1; US20140322806A1.

However, scaffold-free techniques suffer from numerous disadvantages. First, scaffold-free techniques limit the user to studying spheroid growth and viability/toxicity in bulk measurements. Second, scaffold-free techniques do not take into account important aspects of tumor progression such as invasion, metastasis, and angiogenesis in the context of the tumor microenvironment (e.g., stromal cells, vascular cells, macrophages, extracellular matrix).

Scaffold-based techniques build 3D multi-cellular structures for 3D assays from extracellular matrixes, biomaterials, and/or polymeric structures. In the resulting structures, cells collectively respond to matrix, paracrine, and cellular cues to induce invasion, matrix degradation, or differentiation. Scaffold materials include natural, animal-based materials (e.g., basement membrane extract, or Matrigel; collagen), plant-based materials (e.g., alginate), synthetic (e.g., poly-ethylene glycol), or natural-synthetic combination and derivative materials (e.g., methacrylated hyaluronic acid or methacrylic gelatin). See e.g., W. Asghar et al., supra; S. Caliari, J. A. Burdick, A practical guide to hydrogels for cell culture, *Nature Methods*, 2016, 13 (5): 405-414; E. Jabbari, "Three dimensional matrix for cancer stem cells", patent application Ser. No. 14/527,028, October 2014.

Synthetic and synthetic-natural hybrid polymeric biomaterials offer considerable advantages in modular material properties, as well as control over growth factor and binding site presentation and concentration. Modified dextran (e.g., dextran methacylate), gelatin (e.g., gelatin methacrylamide and/or gelatin methacrylate), hyaluronic acid (e.g., hyaluronic acid methacrylate), polyvinyl alcohol (e.g., acrylic acid modified PVA, acrylamide modified PVA) and polyethylene glycol (e.g., polyethylene glycol diacrylate), their derivatives, and combinations, have proven particularly useful in understanding disease progression in 3D cellular models. See e.g., K. Nguyen, J. L. West, Photopolymerizable hydrogels for tissue engineering applications, *Biomaterials*, 2002, 23: 4307-4314; S. Pedron, A. C. Harley, Impact of the biophysical features of a 3D gelatin microenvironment on glioblastoma malignancy, *Journal of Biomedical Research A*, 2013, 101(12): 3404-3415; B. Ananthanarayanan, Y. Kim, S. Kumar, Elucidating the mechanobiology of malignant brain tumors using a brain matrix-mimetic hyaluronic acid hydrogel platform, *Biomaterials*, 2011, 32: 7913-7923. However, there remains a need for apparatuses and methods that quickly and reproducibly fabricate such materials into tissue-mimetic cell culture scaffolds. In other words, apparatuses and processes that form cell culture scaffolds that have properties similar to the in vivo cellular environment by patterning structures (e.g., venous structures) and controlling stiffness, density, porosity, adhesion properties, water content, pH, composition, heat and mass transport etc.

Recently, researchers have used photo-crosslinkable biomaterials for studying cancer progression. Typically, a light-sensitive prepolymer solution is formulated and mixed with cells and polymerized using UV light. A pattern within the matrix may be introduced via a photomask placed between the light source and the material, such that only the light passing through the mask design will crosslink the light-sensitive matrix below. Typically, cancer cells are mixed with the prepolymer solution so that they can be encapsulated within the matrix. See e.g., N. Peela, F. S. Sam, W. Christenson, D. Truong, A. W. Watson, G. Mouneimme, R. Ros, M. Nikkah, A three dimensional micropatterned tumor model for breast cancer cell migration studies, *Biomaterials*, 2016, 81: 72-83. Although this approach is simple, the resulting matrices fail to provide an environment in which cells migrate as if they were in living tissue, Rather, the individual cells may either adhere to one another, to the matrix, or escape the matrix and migrate out of the gel randomly. This random cell response leads to lower reproducibility and complicates measurements of overall tumor growth and invasion.

A second hurdle in current 3D cancer cell culture is enabling long time points for tumor spheroid growth and invasion. Hanging drop studies are practical for only tumor growth and viability studies, without any ability to study tumor cell invasion into extracellular matrix. Spheroid invasion assays are typically performed in Matrigel. However, due to Matrigel's soft (<1 kPa) and easily cell degradable matrix, experiments may not last beyond several days. Cellular processes such as invasion, angiogenesis, and trans-differentiation (whereby tumor cells differentiate into other cell types) may be take weeks. One research group incorporated a tumor spheroid into a polymerized matrix that was wedged between two molds. However, invasion and quantifiable growth were not observed, which may be due to the experimental setup and lack of nutrient transport to the tumor. See e.g., A. Aung, J. Theprungsirikul, H. L. Lim, S. Varghese, Chemotaxis-driven assembly of endothelial barrier in a tumor-on-a-chip platform, *Lab on a chip*, 2016, 16: 1886-1898. Thus, a platform having improved durability and mass (e.g., nutrient, oxygen, carbon dioxide, waste etc.) transport is needed for studying and assaying controlled invasion and tumor growth over long time points.

A third hurdle for cellular assay analysis is studying 3D tumor cell culture in a high-throughput manner (e.g., multi-well plates) without the possibility of culture disruption during liquid media changes (removal via aspiration and re-application via pipetting) and for easy imaging. Currently in both spheroid-only and gel-based assays, sample loss or disruption to the microenvironment is likely to occur, diminishing reproducibility. It is highly necessary to limit any external (e.g., human) errors during media exchange in 3D cell culture.

To address the technical challenges posed by these hurdles, hydrogels have been patterned by extrusion bioprinting into each well, but again using a well-by-well process. These processes are laborious in nature when having to scale into multi-well plates for higher-throughput assays. Cell viability issues arise when cells remain in pre-polymer solution for long durations. And an extrusion process that uses a fine tip causes shear stress that can damage or kill cells, and is limited to using only soft, shearing materials, which are not representative of the tumor microenvironment. It would be beneficial to pattern gels into all wells at once, with the flexibility of material stiffness, to enhance scalability, reproducibility, and customization of the hydrogel structures and increase viability of the cells within and on the gels.

Some progress has been made by forming hydrogels using digital light projection (DLP), stereolithography (SLA), or general photo-patterning, between a glass slide and coverslip, and the resulting gel on glass is added to each well of a multi-well plate. In DLP, the projected image, or mask, is limited by the projector optics, which can cause image clarity and light uniformity issues across the area of the mask.

For example, WO 2015/179572 to Chung et al. discloses a system for 3D microfabrication that projects light toward a light modulator that modulates light responsive to digital masks corresponding to layers of a structure. A series of images corresponding to the digital masks are projected on a photopolymerizable material while a stage controls the optical plane. However, the system requires sophisticated equipment, and fabrication in multi-well plates can only be done using multiple systems or rapidly scanning across multiple wells.

Nikkhah et al. disclose a comparatively simple system in Patent Pub. No. US 2017/0067025. Nikkhah creates a high stiffness construct by cross-linking a first solution that includes cancer cells within a spacer. A second solution is disposed around the high stiffness constructs and cross-linked. Migration of cancer cells from the high stiffness construct to the low stiffness construct can then be observed. However, Nikkhah does not appreciate (1) that hydrogel-based tumor models can be rapidly fabricated within multi-well plates in parallel using a mold to control the height of the hydrogels and (2) that a space between the sides of the hydrogels and the well walls facilitates nutrient transport and exchange of liquid media. See also U.S. Pat. No. 8,906,684 to Bhatia et al.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

It has yet to be appreciated that organ models (e.g., tumor models comprising tumor and non-tumor cells in hydrogels having stiffnesses that mimic tumor and healthy tissue, respectively) may be easily prepared. Thus, there is still a need for apparatuses and processes for making organ, tissue, and tumor models that exhibit more accurate drug responses, especially in high-throughput diagnostics and therapeutic assays.

SUMMARY OF THE INVENTION

The inventive subject matter provides methods for patterning multi-layer hydrogels into one or more wells of a multi-well plate via photopolymerization in combination with a pillar inserted into each of the wells. For example, such methods can be used to pattern tumor cells in a hydrogel having a stiffness or pattern that corresponds to tumors in vivo, or to generate organoids of controlled configuration within the wells of a plate.

One embodiment of the inventive concept is a method of forming a hydrogel in a well by adding a first prepolymer to the well, inserting a first post (with a surface that contacts the first prepolymer once inserted) into the well, and exposing the first prepolymer to a photopolymerizing light to initiate polymerization of the first prepolymer. A wash step can be performed (for example, using PBS or culture media) to remove excess first prepolymer from the well. These steps can be repeated using a second prepolymer and a second post to generate an additional polymer within the well, and can be followed by adding liquid media to the well. The posts can have different cross sections, and the contacting surface of the post can have different textures or patterns, for example corresponding to different features of organoids or tumor models. The prepolymers used can include different cell populations. For example, the first prepolymer can include tumor cells such as tumor cells obtained from primary culture, tumor cells obtained from cell lines, cancer stem cells, spheroid, and/or multi-cellular aggregate. In some embodiments cells of the second prepolymer are nontumor cells, such as stromal cells, endothelial cells, pericytes, organ-specific cells t-type, cancer associated fibroblasts, lymphocytes, macrophages, endothelial cells, dendritic cells, bone marrow derived cells, mesenchymal stem cells, endothelial progenitor cells, normal epithelial cells, and/or granulocytes. In some embodiments the cells of the first prepolymer and/or the second prepolymer can be cardiomyocytes, cardiac fibroblasts, endothelial cells, vascular smooth muscle cells, parietal cells, podocytes, mesangial cells, keratinocytes, fibroblasts, and melanocytes, hepatocytes, fibroblasts, endothelial cells, and Kupffer cells, and/or stem cells.

The light used for photopolymerization steps can pass through different passageways. For example, light used for the first photopolymerization step can pass through a first light passageway and light used for a second photopolymerization step can pass through a second light passageway. These different passageways can provide illumination to different portions of the well. In some embodiments the above steps can be carried out on more than one well of a plate. In such embodiments each well can be illuminated by individual, controlled light sources, which are controlled to provide even illumination between the different wells. In other embodiments a single, collimated light source can be used.

Preferably, tumor models produced using the inventive apparatuses adhere to the bottom of each well of the multi-well plate. A space between side surface(s) of the tumor model and the walls of each well allow for liquid media to contact both top and side surfaces of the tumor model. The ability to exchange the media with minimal hydrogel disruption more closely replicates the in vivo tumor environment and increases the length of time over which the tumor model can be cultured. The generation of such tumor models can be useful in studying metastasis in patient tumors and known cell lines, and to test therapeutic agents in a high throughput manner.

Apparatuses according to the inventive subject matter comprise a light source, a photomask, a holder that aligns the photomask and the multi-well plate, and a mold that configures surfaces of hydrogels in the various wells of the multi-well plate.

Suitable light sources emit light having energy (wavelength(s)) and power that initiates polymerization and/or crosslinking of prepolymer (e.g., monomers/macromers). Although use of a single, diffuse light source (e.g., a mercury or other light bulb) is contemplated, preferred embodiments comprise an array of light-emitting diodes ("LEDs"). Each LED of the LED array is positioned to illuminate one well of a multi-well plate. For example, when a multi-well plate is stacked on top of a holder, photomask, and light source, each LED of the LED array is centered under one well of the a multi-well plate. Advantageously, LED's emit less heat than incandescent bulbs, decreasing the likelihood that the heat will damage or kill the cells in the pre-polymer mixture. It should be appreciated that the light source emits light in the UV and/or visible ranges to initiate hydrogel polymerization using photoinitiators that have excitation wavelengths in the UV and/or visible ranges, respectively. For example, a light source that has peak emission wavelengths of 300-500 nm, 350-450 nm, and preferably about 365 or 405 nm are suitable for use in the inventive apparatus. The emission wavelength can be further tuned using filters and/or monochromators.

The light source can be powered by either battery or electricity and can be controlled using simple switches, timers, or programmed controllers (e.g., an Arduino® controller). In an exemplary embodiment of the inventive subject matter, a controller controls light intensity, wavelength, on-time, and/or other lighting parameters. When an LED array is used, the controller can individually control such parameters for each LED. Optionally, the controller can be configured to automatically turn the light source on when the mold is inserted in the multi-well plate.

Contemplated multi-well plates include those with which researchers are already familiar and those that can be used in existing imaging equipment, for example MatTek™ glass bottom plates having, e.g., 35 mm, 50 mm, 60 mm, or 100 mm dishes having microwell diameters of 7 m, 10 mm, 14 mm, 20 mm, or 30 mm. The inventors further contemplate that the inventive apparatuses could be adapted for use with the Thermo Scientific™ Nunc™ Lab-Tek™ II Chamber Slide™ System (having 1, 2, 4, or 8 wells per slide system), Greiner Sensoplates, and/or Matsunami glass bottom dishes.

Photomasks allow light to pass through the pre-polymer to initiate polymerization. Contemplated photomasks have opaque regions to block light and light passageways (e.g., holes or transparent regions) to allow light to illuminate the multi-well plate and prepolymer solution. For example, one light passageway allows light to illuminate a central portion of the bottom of a well while excluding an edge region. Conversely, another light passageway allows light to illuminate an edge region of the bottom of a well, but excludes the central portion. The photomask can also include light passageways that allow light to illuminate the bottom of each well, including the edges. This would result in hydrogels that extend up the sides of the posts and the walls of each well. Such hydrogels can also be obtained when the apparatus is used without a photomask. Alternatively, light passageways can be partially opaque (translucent, but not transparent) in some areas to offer further flexibility in resulting polymerization, gelation properties, and gel structures.

In one exemplary embodiment, a photomask having a diameter less than the internal diameter of the wells is used to create a tumor cell-containing hydrogel. Then, a second photomask having a light passage with a larger diameter is used to polymerize a non-tumor cell-containing outer layer that contacts the top and sides of the tumor cell-containing hydrogel. In another exemplary embodiment of the inventive subject matter, the same photomask is used in the first and second photopolymerization steps to form a second hydrogel layer having the same diameter as the first hydrogel layer on the first hydrogel layer, without fully encasing the sides of the first layer.

The size of each light passageway can also be varied. Contemplated light passageways can be configured to transmit light to no more than 50%, 55%, 60%, 65%, 70%, 75%, 80%, 85%, 90% etc. of the cross-sectional area of the bottom of one or more wells. Light passageways can have a variety of shapes, including, but not limited to: lines, circles, ovals, triangles, squares, pentagons, hexagons, dot arrays, venous structures, etc.

Holders align the photomasks and multi-wells plate above the light source. To fabricate multilayer tumor models, one photomask is used to pattern each layer. Therefore, the holder allows for successive photomasks to be positioned under the multi-well plate during each step of the tumor model fabrication process. Holders may have a variety of suitable configurations. For example, a holder may comprise a recess, slot, drawer, etc. configured to retain the photomask. To align multi-well plates with the photomask, a holder also includes a recess, slot, or other mechanism for retaining multi-well plates.

Molds control the thickness and the contours of the top surface of each layer of the tumor models. Molds have posts that dip into prepolymer solution dispensed into each well of the multi-well plate. The diameter of each post allows enough space between each post and the walls of each well to allow the prepolymer mixture displaced by the post to rise in each well. To control the thickness of each layer, the bottom end of each post is positioned at a distance from the bottom of a well and molds the top surface of the resulting polymer structure. Employing molds improves consistency of hydrogel height and makes the top layer of each polymer flat. Whereas without molds, the top surface of each layer may curve with the meniscus of the prepolymer mixture. These advantageous effects are achieved, because the posts come in contact with the prepolymer solution resulting in a planar polymerization plane and reach through the oxygenated zone of the prepolymer mixture where polymerization would be quenched. The mold may also reflect light, enhancing polymerization.

Molds can be disposable or reusable (sterilizable). The number of posts can be selected to match the number of wells in the multi-well plate. The size and shape of each post can also be varied. For example, the posts can have different lengths and/or different horizontal cross-sections.

In one embodiment of the inventive subject matter, the apparatus is assembled by simply stacking each element. Another embodiment includes a housing configured to orient light from the light source toward the multi-well plate. Optionally, the housing may also be configured to control hydrogel thickness by controlling the distance between the bottom of mold posts and the bottom of the wells. For example, the housing can include rails, tension rods, slots, adjustable pegs, a set of height adapters (e.g., inserts having different thicknesses), a screw jack, a servo, an actuator, or other structure configured to lower/raise the mold such that the post(s) dip into the well(s) to set distance(s) from the bottom of the well(s).

Yet another embodiment of the inventive subject matter includes a second holder that retains the mold and adjusts relative positions of the mold and the plate. Such holders can also be configured to removably retain molds, so that different molds can be used in the apparatus including: disposable or reusable molds, molds with differing numbers of posts for use with multi-well plates having different numbers of wells, and/or different post designs.

An enclosure can be used to limit operator's exposure to UV light. For example, the enclosure could be disposed around at least a portion of the multi-well plate to shield the operator from light leakage. Contemplated enclosures are black or transparent. Transparent enclosures absorb/filter harmful wavelengths of light but allow the operator to view the process.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 3A shows a schematic representation of photopolymerization using the inventive apparatus.

FIG. 3B shows a close-up view of one well of the scheme shown in FIG. 3A.

FIG. 3C shows a hydrogel in liquid media in the well shown in FIG. 3B.

FIGS. 4A-C show exemplary photomask designs.

FIGS. 5A-B show exemplary light sources.

DETAILED DESCRIPTION

The inventors have devised an apparatus for preparing a high-throughput 3D cellular assay for studying tissue growth, viability, and high throughput drug screening. For example, tumor assays for studying growth, viability, and invasion and migration through an extracellular matrix that is representative of the tumor microenvironment in terms of composition and stiffness. One should appreciate that the disclosed apparatus and techniques provide many advantageous technical effects including the ability to reproducibly tune the composition and stiffness of in vitro hydrogels to mimic the extracellular matrix microenvironment of tumors in vivo. Additionally, the planar hydrogel surfaces formed using the inventive apparatus enable superior real-time brightfield and fluorescence imaging.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Figure 1A:
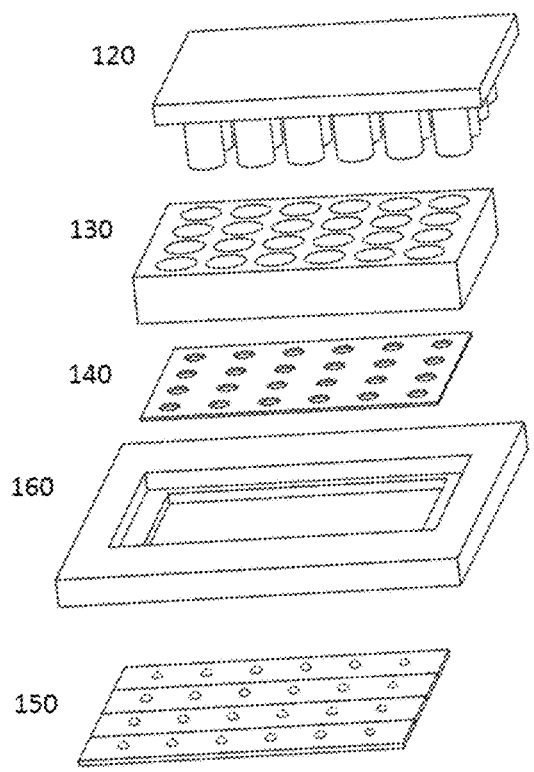
FIG. 1A is an exploded view of an apparatus and a 24-well plate.
Figure 1B:
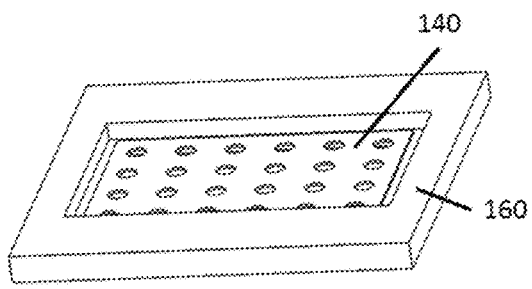
FIG. 1B shows a photomask nested in a holder.

FIG. 1A shows an exploded view of the elements one embodiment of the inventive subject matter. The apparatus includes mold 120, multi-well plate 130, photomask 140, light source 150, and holder 160. The multi-well plate shown is a standard 24-well plate, so the photomask 140 has 24 light passages, and light source 150 has 24 LEDs. FIG. 1B shows photomask 140 nested in holder 160. When the elements are stacked, the holder aligns the light passages of photomask 140 and each LED of light source 150 with the wells of the 24-well plate.

In addition to 24-well plates, the inventor contemplates that apparatuses can be modular in design such that various elements are designed to work with different multi-well plates (e.g., 6-well, 12-well, 24-well, 48-well, 96-well, 384-well, 1536-well plates). For example, the number of posts in mold 120, the number of light passages in photomask 140, and the number of LEDs in light source 150 typically match the number of wells in the multi-well plate. In addition to multi-well plates apparatus designs can be configured for use with MatTek glass bottom dishes, Thermo Scientific™ Nunc™ Lab-Tek™ II Chamber Slide™ Systems, and/or Matsunami glass bottom dishes.

Figure 1C:
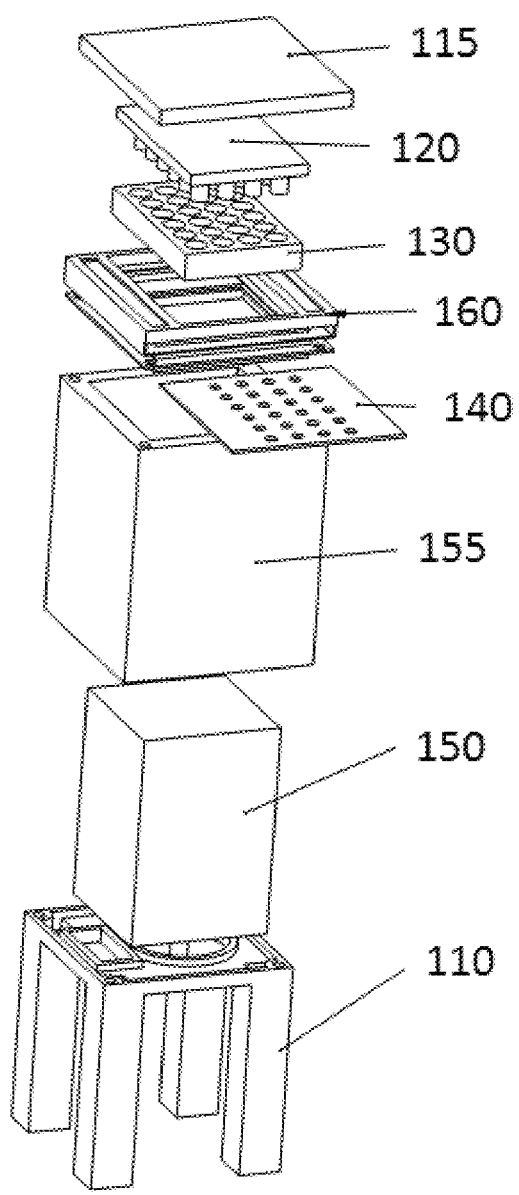
FIG. 1C shows another embodiment of an apparatus according to the inventive subject matter and a 24-well plate.

The apparatus shown in FIG. 1C includes housing 110, enclosure 155, and top enclosure 115. Holder 160 includes a slot for inserting photomask 140. Advantageously, different photomasks can easily be inserted/removed from the slot in holder 160 to form different hydrogel layers. Rather than a slot, holder 160 can include a drawer for removably retaining different photomasks.

Figure 2A:
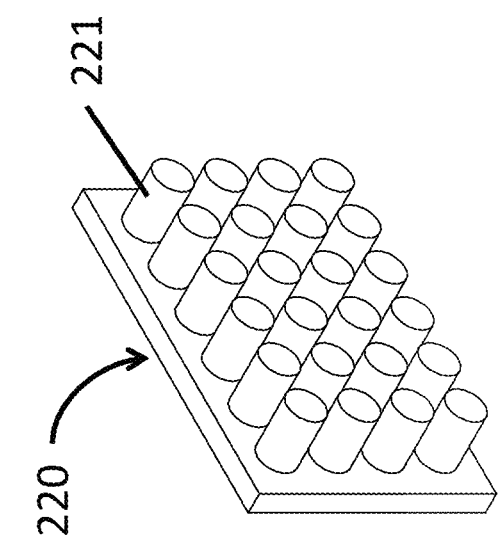
FIGS. 2A-D shows perspective, side, and bottom views of a mold for a 24-well plate.
Figure 2C:
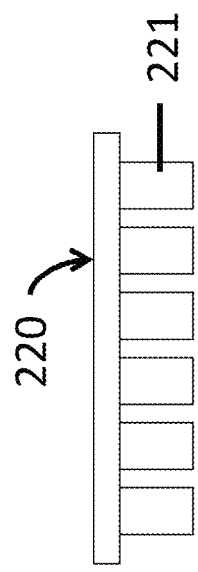
Figure 2B:
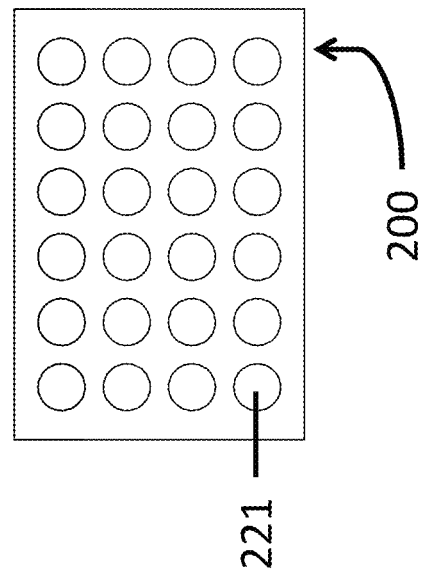
Figure 2D:
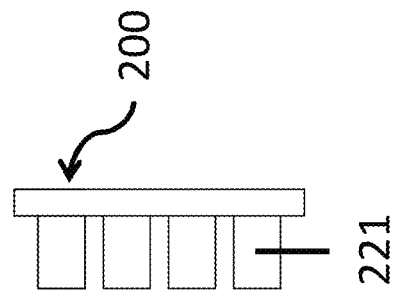

FIGS. 2A-D show various views of mold 220 and posts 221. FIG. 2A is a perspective view. FIG. 2B shows a bottom view of mold 220, looking down the axis of posts 221. FIGS. 2C and 2D show side views of mold 220 having 6 and 4 posts 221, respectively. Suitable molds do not substantially adhere to the hydrogel after polymerization. For example, molds made of polydimethylsiloxane ("PDMS") or Teflon® release the hydrogels after polymerization without damaging them. Alternatively, molds can comprise a nonstick coating, (e.g., PDMS or Teflon®). The apparatus may be used without the mold. However, molds improve the reproducibility of hydrogel fabrication by molding the surface and controlling the height of the hydrogels.

Although the molds shown have posts with smooth, planar bottom surfaces, the bottom of each post can also be textured and/or patterned to mold different organoid/tissue structures. For example, the bottom of each post can comprise channel molds to yield hydrogels having channels that mimic vascular structures. See e.g., WO2016141137A1 to Lewis et al. In another example, the bottom of each post can comprise a renal cortex mold that forms an organoid model of the renal cortex after polymerization of one layer, then the medulla can be polymerized in the next layer or vice versa. The inventive apparatus can also be employed to simultaneously fabricate and seed tissue engineered organs such as the colon, esophagus, and pancreas models as described in U.S. patent application Ser. No. 10/150,828 to Grikscheit et al. In yet another exemplary embodiment of the inventive subject matter, the mold can comprise a mold for honey comb structures to form liver tissues as described by Shepherd et al. in US20160272946A1.

A schematic representation of fabricating a hydrogel using the inventive apparatus is shown in FIGS. 3A-C. Each well 331 of multi-well plate 330 holds prepolymer 381. Mold 320 is placed on top of multi-well plate 330. Posts 321 dip into prepolymer 381 in each well 331. Light from light source 350 passes through light passages 341 of photomask 340, initiating polymerization of prepolymer 381. Polymerization zone 382 is shown in close-up FIG. 3B. After the polymerization step is complete, excess prepolymer 381 is washed away (e.g., by aspiration using PBS), and liquid media 390 is added to well 331 and contacts the sides and top surface of hydrogel 383. Although a single hydrogel layer is shown, additional polymerization steps can be performed to add additional hydrogel layers.

Exemplary hydrogel prepolymers comprise dextran, collagen, gelatin, hyaluronic acid, polyvinyl alcohol, and/or polyethylene glycol. The prepolymer and the resulting hydrogel can also comprise an extracellular matrix, an extracellular matrix component, and/or an extracellular matrix derivative. One having ordinary skill in the art would appreciate that the extracellular matrix component may include laminin, fibronectin, elastin, and/or fibrin. The prepolymer solution can also comprise cell binding and signaling peptides and proteins. The peptide and/or protein component can include one or more of Streptavidin, biotinylated-proteins, acrylated-RGD peptide, VEGF protein, and so on. See e.g., Gjorevski N. et al. Designer matrices for intestinal stem cell and organoid culture. *Nature* 2016, 539, 560-564.

The greater the degree of crosslinking between polymer chains, the greater the hydrogel stiffness. The inventors contemplate that the stiffness of a tumor cell-containing hydrogel can range from 1 Pascals (Pa) to 100,000 kiloPascals (kPa), including the end points. For tumor models, the stiffness of the tumor cell-containing hydrogel is between 10 Pa and 100 kPa, and even more preferably between 1 kPa and 40,000 kPa, inclusive. Bone and cartilage models have stiffnesses that may exceed 100 kPa. See e.g., WO2016142323A1 to Schaufelberger et al. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

In further regard to hydrogel stiffness, any suitable means of crosslinking is contemplated, for example, chemical or physical crosslinking. Preferably, chemical crosslinking is achieved by photocrosslinking. The inventors contemplate that suitable photoinitiators are UV or visible light-responsive, soluble, and minimally cytotoxic before and after polymerization. As used herein the term minimally cytotoxic means that the photoinitiator kills no more than 50%, and preferably no more than 10%, of the tumoral or nontumoral cells disposed in the prepolymers used to prepare the first and second matrices as measured after polymerization. For example any Irgacure® photoinitiator may be suitable.

In this schematic, the thickness of the resulting hydrogel, 383 (FIG. 3C) is determined by the length of each post 321. The thickness of hydrogel 383 can be controlled using molds having posts with different lengths, using spacers, holders, etc.

FIG. 4A shows a schematic representation of photomask 440 with circular light passages 441 having a variety of diameters. For example, the hydrogel pattern can comprise a plurality of circles each having a width of 25-5000 microns and a height of 25-2000 microns. Photomasks can be made of opaque plastic or metal with cutout areas that serve as light passages. Photomasks can also be made from transparency film (e.g., with silver halide ink) or soda lime/quartz (with chrome). A photomask may also comprise light passageways, which comprise a plurality of irises that can be adjusted to different diameters.

FIG. 4B is a schematic representation of photomask 440 having light passages 441 having different shapes and sizes. Although circles, triangles, squares, and hexagons are shown, the photomask can comprise a plurality of polygons (e.g., squares, rectangles, pentagons, hexagons, heptagons, octagons, etc.), wherein each polygon of the plurality of polygons has a width of 50-5000 microns and a height of 50-2000 microns.

FIG. 4C shows a photomask having a plurality of linear light passages. Exemplary photomasks yield hydrogel patterns that comprise a plurality of lines each having a width of 25-5000 microns and a height of 25-2000 microns.

Figure 5B:
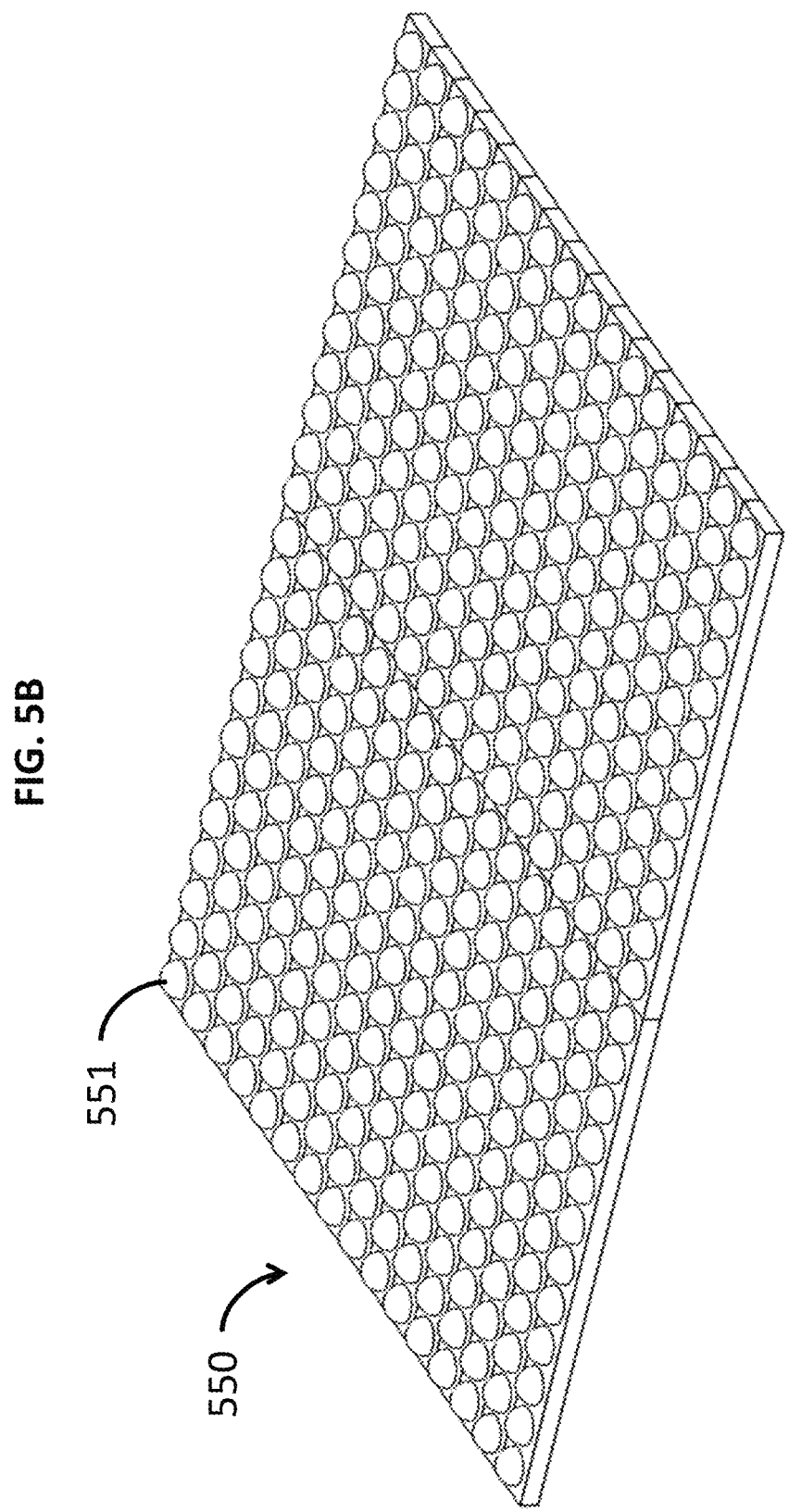

FIG. 5A shows light source 550 having 96 LEDs 551, and FIG. 5B shows light source 550 having 384 LEDs 551. It should be appreciated that the number of LEDs need not necessarily match the number of wells in the multi-well plate used in the apparatus. For example, a 96 or 184 LED array may provide sufficiently uniform light to produce uniform hydrogels in a 24-well array. Conversely, 24 LEDs can be configured to reproducibly produce uniform hydrogels in multi-well arrays having more than 24 wells by varying the direction of the light emitted, the distance from the light source, and the photomask design. Optionally, a heat skink may be included to limit temperature changes and damage to the LEDs, which is preferable for some prepolymer solutions.

The apparatus can further comprise a plurality (e.g., a bundle or an array) of optical fibers (and any necessary couplers/optical equipment). In some embodiments, hydrogel patterning within the multi-well plate (or other container) can be achieved by illuminating the prepolymer via individually (or selectively) addressable optical fibers, without a photomask. Advantageously, the light source can be positioned remote from the cell laden prepolymer, decreasing the risk that heat from the light source will accelerate polymerization or damage the cells.

In yet another embodiment, the light source and mold are configured to illuminate the prepolymer from above. For example, the mold can have posts made of a light conducting material, such as poly(methyl methacrylate) (e.g., Lucite), quartz, or glass to deliver light to the prepolymer in addition to controlling hydrogel height/thickness. An opaque coating on the mold can be used to control the pattern of light emitted from the posts. For example, the coating may cover the portion of the mold from which each post extends as well as the side surfaces of each post, leaving uncoated portions for light entry and exit from the mold. The bottom of each post can further be patterned with lines, polygons, or other shapes in the manner described above in regard to photomasks.

To prepare tumor models using apparatuses according to the inventive subject matter, a first hydrogel is patterned in each well of a multi-well plate using photolithography, wherein the first hydrogel has a first stiffness and encapsulates a tumor cell. A second hydrogel is patterned in each well of the multi-well plate using photolithography and at least partially contacts the first hydrogel. The second hydrogel has a second stiffness, different from the first stiffness and encapsulates a non-tumor cell. The inventive subject matter further includes tumor models that optionally feature a third hydrogel and a third cell type either encapsulated in the third hydrogel or disposed between the second and third hydrogels.

With respect to the tumor cells, contemplated tumor cells include tumor cells from primary culture, tumor cells from cell lines, and/or cancer stem cells. In preferred embodiments, the tumor cell further comprises a plurality of tumor cells, which form a spheroid.

Suitable nontumoral cells include a stromal cell, an endothelial cell, a pericyte, and/or an organ-specific cell t-type. Therefore, the nontumor cell can comprise one or more of cancer associated fibroblasts, lymphocytes (T cells, B cells, and/or natural killer cells), macrophages, endothelial cells, dendritic cells, bone marrow derived cells, mesenchymal stem cells, endothelial progenitor cells, normal epithelial cells, and granulocytes (eosinophils, basophils, and/or neutrophils).

To model cardiac tissues, the cells may comprise cardiomyocytes, cardiac fibroblasts, endothelial cells, and/or vascular smooth muscle cells, etc. Kidney models can comprise parietal cells, podocytes, and/or mesangial cells. Skin models can comprise keratinocytes, fibroblasts, and melanocytes. Liver models can comprise hepatocytes, fibroblasts, endothelial cells, and Kupffer cells. See e.g., US20160272946A1 to Shepherd et al. Neurons and glial cells can be employed in brain tissue models. In any tissue model, stem cells (adult, embryonic, induced pluripotent, or other stem cells) can be included to further mimic the target cellular microenvronment and/or to regenerate tissue-specific cells.

The cells may be labeled with fluorescent dyes or proteins (e.g., green-fluorescent protein, red-fluorescent protein, CellTracker™, mCherry, and so on) to distinguish individual cell populations and to track tumor growth and invasion in the context of the microenvironment cells.

The inventive subject matter offers several advantages: spatial patterning of chemically (and photochemically) crosslinkable materials with a broad range of material properties (e.g., stiffness and composition) enables a more realistic extracellular matrix for tumor and non-tumor compartments of a tumor assay to match physiological conditions in vivo; sequential patterning of multiple cell types on the tumor microenvironment (e.g., tumor vs. non-tumor cells) enables more controlled evolution of cell interactions; precise placement of tumor and non-tumor cell types in 3D enables observation of tumor progression into non-disease tissue, and allows dissection of various components of the microenvironment, including a changing ECM, the role of various cell types, and tumor response to various drug treatments; the evolving tumor growth and invasion through the matrix and onto the planar matrix surface enables image clarity and quantifiable measurements of growth, viability and invasion in response to drug treatment; 3D gel constructs fabricated in a well of a tissue culture dish, glass slide, or multi-well plate where there is a space between the gel and well wall enables efficient liquid media exchange during aspiration and pipetting and minimal disruption to the gel.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of forming a hydrogel in a first well of a multi-well plate, comprising;
   providing an apparatus comprising:
     a light source;
     a holder configured to align a photomask and the multi-well plate;
     an enclosure at least partially disposed about the multi-well plate and configured to limit light exposure to an operator; and
     a mold having first post sized and dimensioned to fit into the first well,
   wherein the light source is positioned to illuminate the first well through the photomask, with sufficient energy to initiate polymerization of a prepolymer to form the hydrogel;
   positioning a photomask in the apparatus;
   placing the multi-well plate in the holder;
   dispensing a first prepolymer into the first well;
   inserting the first post into the first well, wherein the first post comprises a first contact surface that contacts the first prepolymer upon insertion;
   exposing the first prepolymer to a first illumination, thereby initiating polymerization of the first prepolymer;
   performing a wash step to remove excess first prepolymer;
   dispensing a second prepolymer into the first well;
   inserting a second post into the first well, wherein the second post comprises a second contact surface that contacts the second prepolymer upon insertion;
   exposing the second prepolymer to a second illumination, thereby initiating polymerization of the second prepolymer; and
   dispensing a liquid media into the first well.

2. The method of claim 1, wherein the first contact surface and the second contact surface have different cross sections.

3. The method of claim 1, wherein the wash step comprises aspiration with phosphate buffered saline (PBS) or cell culture media.

4. The method of claim 1, wherein the first contact surface comprises a first texture or pattern.

5. The method of claim 4, wherein the first texture or pattern is configured to mold a first organoid or a first tissue structure.

6. The method of claim 1, wherein the second contact surface comprises a second texture or pattern.

7. The method of claim 6, wherein the second texture or pattern is configured to mold a second organoid or a second tissue structure.

8. The method of claim 1, wherein the first prepolymer comprises a plurality of first cells and the second prepolymer comprises a plurality of second cells.

9. The method of claim 8, wherein the plurality of first cells are tumor cells.

10. The method of claim 9, wherein the tumor cells are selected from the group consisting of tumor cells obtained from primary culture, tumor cells obtained from cell lines, and cancer stem cells.

11. The method of claim 10, wherein the plurality of tumor cells comprise a spheroid, or multi-cellular aggregate.

12. The method of claim 8, wherein the plurality of second cells are nontumor cells.

13. The method of claim 12, wherein the nontumor cells are selected from the group consisting of stromal cells, endothelial cells, pericytes, organ-specific cells t-type, cancer associated fibroblasts, lymphocytes, macrophages, endothelial cells, dendritic cells, bone marrow derived cells, mesenchymal stem cells, endothelial progenitor cells, normal epithelial cells, and granulocytes.

14. The method of claim 8, wherein at least one of the plurality of first cells and the plurality of second cells are selected from the group consisting of cardiomyocytes, cardiac fibroblasts, endothelial cells, vascular smooth muscle cells, parietal cells, podocytes, mesangial cells, keratinocytes, fibroblasts, melanocytes, hepatocytes, fibroblasts, endothelial cells, and Kupffer cells, and a stem cell.

15. The method of claim 1, wherein the first post and the second post are configured to form a tissue engineered organ or a tissue structure, and wherein the first prepolymer comprises a plurality of third cells and the second prepolymer comprises a plurality of fourth cells.

16. The method of claim 15, wherein at least one of the plurality of third cells and the plurality of fourth cells are selected from the group consisting of cardiomyocytes, cardiac fibroblasts, endothelial cells, vascular smooth muscle cells, parietal cells, podocytes, mesangial cells, keratinocytes, fibroblasts, melanocytes, hepatocytes, fibroblasts, endothelial cells, neurons, glial cells, and Kupffer cells, and a stem cell.

17. The method of claim 1, wherein the first illumination occurs through a first light passageway and the second illumination occurs through a second light passageway.

18. The method claim 17, wherein the first light passageway provides illumination of a first area of the first well and the second light passageway provides illumination of a second area of the first well.

19. The method of claim 1, comprising the additional steps of:
   dispensing a third prepolymer into a second well of the multiwell plate;
   inserting a third post into the second well, wherein the third post comprises a third contact surface that contacts the first prepolymer upon insertion; and
   exposing the third prepolymer to a third illumination during the first illumination, thereby initiating polymerization of the third prepolymer.

* * * * *